(12) United States Patent
Takahashi (10) Patent No.: US 7,713,058 B2
(45) Date of Patent: May 11, 2010

(54) DENTAL MIRROR, AND AN INTRAORAL CAMERA SYSTEM USING THE SAME

(76) Inventor: Atsushi Takahashi, 20-15-1, Kizaki, Tsuruga, Fukui (JP) 914-0814

( * ) Notice: Subject to any disclaimer, the term of this patent is extended or adjusted under 35 U.S.C. 154(b) by 557 days.

(21) Appl. No.: 10/628,664

(22) Filed: Jul. 28, 2003

(65) Prior Publication Data
US 2005/0026104 A1 Feb. 3, 2005

(51) Int. Cl.
*A61C 1/00* (2006.01)
*H04N 7/18* (2006.01)
(52) U.S. Cl. .......................................... 433/31; 348/66
(58) Field of Classification Search .................. 433/29, 433/30, 31; D14/371, 374; 359/839, 882; 348/66
See application file for complete search history.

(56) References Cited

U.S. PATENT DOCUMENTS

| 3,884,222 A | * | 5/1975 | Moore ......................... 600/188 |
| 4,568,281 A | * | 2/1986 | Harvey et al. ................. 433/30 |
| 5,049,070 A | * | 9/1991 | Ademovic .................... 433/29 |
| 5,251,025 A | * | 10/1993 | Cooper et al. ................. 348/66 |
| 5,373,317 A | * | 12/1994 | Salvati et al. ................. 348/65 |
| 5,429,502 A | * | 7/1995 | Cooper et al. ................. 433/29 |
| 5,741,132 A | | 4/1998 | Usui et al. |
| 5,745,165 A | * | 4/1998 | Atsuta et al. .................. 348/65 |
| 5,951,284 A | * | 9/1999 | Lake ........................... 433/31 |
| 6,201,880 B1 | * | 3/2001 | Elbaum et al. .............. 382/100 |
| 6,276,934 B1 | * | 8/2001 | Rakocz ........................ 433/29 |
| 6,956,601 B2 | * | 10/2005 | Squilla et al. ................. 348/65 |
| 2002/0067408 A1 | * | 6/2002 | Adair et al. ................... 348/76 |
| 2002/0118279 A1 | * | 8/2002 | Spoonhower et al. ......... 348/66 |
| 2003/0228553 A1 | * | 12/2003 | Mandelkern et al. .......... 433/29 |

FOREIGN PATENT DOCUMENTS

| JP | 7-318849 | 12/1995 |
| JP | 8-112252 | 5/1996 |
| JP | 9-327436 | 12/1997 |
| JP | 2001-061779 | 3/2001 |

* cited by examiner

*Primary Examiner*—Ralph A Lewis
(74) *Attorney, Agent, or Firm*—Quintero Law Office (57) ABSTRACT

An intraoral camera system is disclosed, which includes a dental mirror having a aperture for transmitting light therethrough, the aperture being provided in the center or any other part of the mirror by removing a reflective material therefrom. A CCD camera is secured on a back surface of the dental mirror in such a manner that the aperture coincides with its incident portion coincides with aperture in the dental mirror. A hand mirror shaped monitor is also provided for displaying image data received from the CCD camera via cable or radio, and a server is also provided that is capable of storing and outputting the image data any time onto the monitor, wherein even though a patient is laid down on a chair in a horizontal position, the patient or a third party can utilize the hand mirror shaped monitor to view an image which is very close to the image that a dentist views through reflection from the dental mirror having said CCD camera built therein.

17 Claims, 5 Drawing Sheets

DENTAL MIRROR, AND AN INTRAORAL CAMERA SYSTEM USING THE SAME

TECHNICAL FIELD

The present invention relates to a technology that assists doctors or dentists to obtain informed consent from their patients by providing a visual aid that allows patients to view, regardless of their body position, the area in the patients' mouth which the patients' cannot see with only a single reflector.

RELATED ART

Generally, when a dentist or doctor discusses the situation of a problem area which his or her patient cannot directly see, the dentist or doctor uses two reflectors or otherwise uses a liquid crystal or CRT monitor along with an input device such as a CCD.

Nonetheless, as described above, a dentist or doctor examines and treats the patient who is in a horizontal position laid in a bed. When the dentist explains the condition of the problem area to his or her patient using two dental mirrors while the patient views the areas such as anterior teeth, lingual surface, posterior teeth, and occlusal surface with a hand mirror, the dentist has no way of knowing that the patient is accurately viewing the target projected by the hand mirror. Ensuring that the patient views the target area always requires extraordinary skills based on the dentist's or doctor's experience and intuition.

The situation is worse when one tries to project the patient's front teeth or face on a liquid crystal screen in the same manner one projects the image on a reflector. A CCD camera is installed at a point on the periphery of the liquid crystal screen, in other words, an image is captured at a point above, below, right, or left of the object causing distortion of the captured image.

The same is true when the dentist explains the condition of a disease using the liquid crystal or CRT monitor along with an input device such as a CCD camera. The patient can see the image captured by a CCD camera only on a liquid crystal or CRT monitor. As a result, the monitor must be installed above the head of the patient who is in a horizontal position on a bed. When the patient holds a compact liquid crystal monitor or the like, the dentist must have another monitoring facility to confirm the location of his CCD camera. In addition, the dentist must further shift his or her line of view from the target area inside the patient's mouth to the monitor to confirm the location of his or her CCD camera, even though the dentist should directly view the patient's mouth. Manipulation of the above input and output devices to obtain the target image for the patient without directly viewing the actual situations thereof requires extraordinary skill.

Often, a mirror or the surface of a camera lens fogs up due to the patient's breathing or cooling water supplied to polishing tools.

SUMMARY OF THE INVENTION

To overcome at least one of these problems, the present invention intends to provide a means to convey the image a dentist directly views to his or her patient without shifting his or her line of view from the patient when the dentist describes the condition of a disease in a problem area that the patient cannot directly see while he or she is laid on a bed for examination and treatment. The present invention also intends to provide an intraoral camera system with a defogging mirror and camera lenses.

More specifically, in an example of the present invention, reflective material is removed from a dental mirror at a center or any other area of its back surface to transmit light therethrough and a CCD camera is attached thereto. The image data received from the CCD camera is sent to a hand-mirror shaped monitor via radio or cable. In this way, even though the patient is laid horizontally on a bed for examination or treatment and is in a position where he or she is unable to see the target area, the dentist can provide the target image in the same field of view to the patient that the dentist views in a dental mirror without shifting his or her line of view from the patient's mouth. In an example of the present invention, the image is also stored in a server to make it available at any time.

The dental mirror comprises a CCD camera attached to the center of the back surface of a dental mirror, a gear attached to the same rotary shaft as that of the CCD camera such that the gear rotates around the CCD camera, a battery driven micromotor, a battery positioned inside the dental mirror holder, a gyro sensor for outputting a signal that incorporates a motion of the gyro sensor with that of the gear on inclination of the dental mirror to a horizontal plane or floor, and a control mechanism for controlling the rotation angle of the CCD camera in accordance with the signal from the gyro sensor. In this way, even though the dentist continuously moves the dental mirror longitudinally or horizontally to capture images of the patient's teeth, the image of the target is captured at a preset angle, which is constant. Thus, the dentist can easily determine which teeth are on the liquid crystal screen regardless of the angle at which the dentist holds or inserts the dental mirror in the patient's mouth.

The hand mirror shaped monitor is very compact so that the patient can hold it wherever it is easy for the patient as he or she lies in a horizontal position on a bed. The monitor further comprises a liquid crystal plate having a portion at the center where some liquid crystal is removed to transmit light therethrough, and a CCD camera, which is provided on a back surface of the liquid crystal plate, which allows capturing a frontal image of the front teeth or face at the same level as the line of view through the incident portion where some liquid crystal material is removed. This configuration provides an image that is free from all directional distortion on the CCD dental mirror, which is as manageable as a regular mirror. The hand mirror shaped monitor having an image conversion processor is capable of inverting the data input from the center CCD camera in terms of backside forward and upside down or rotating clockwise or counterclockwise. It is therefore capable of reproducing on a liquid crystal screen an upright image, not the inverted image that a regular mirror produces but the same image of the face that a third party can see with his or her eyes.

Further, the dental mirror portion can be used as a light source by illuminating the target area with lighting from a conventional surgical lighting system provided on a dental chair.

Another type, wherein a dentist directly attaches a CCD camera to a dental mirror before insertion into a patient's mouth, may be modified to an alternate type having a CCD camera. In this alternate type, one end of the optical fiber may have an incident portion coinciding with the portion on the back surface of the dental mirror from which a reflective material is removed, whereas the other end of the optical fiber may have a CCD camera for inputting the field of view obtained at the incident portion.

In this alternate type having a CCD camera, the CCD camera is located in front of the hand mirror shaped monitor and usually, an image is provided thereon via an optical fiber.

When the optical fiber is removed, the CCD camera directly displays the frontal view thereof, just like the way a generic hand mirror does.

To obtain a light source for this system, a dentist may use a dental mirror to reflect light from the surgical lighting system attached to the dental chair. Alternately, he or she may use a halogen lamp light source to illuminate the field of view through the taper fiber portion of the optical fiber.

Nonetheless, the camera lens surface of the intraoral camera system described above often collects moisture due to the patient's breathing or cooling water supplied to a polishing tool. To resolve this problem, an airway pipe having a jet nozzle pointing toward the CCD camera and optical fiber's incident portion, is provided coaxially with the dental mirror holder to inject air into the surface of the dental mirror, CCD camera, and optical fiber's incident portion to blow away moisture, saliva, cooling water and the like, thereby enhancing the field of view.

When the patient is uncomfortable with dryness due to air injected into his or her mouth, the opposite end of the jet nozzle may be hooked up with a suction port connected to a vacuum device to suck out the injected air. The patient's mouth can thus be protected from drying.

BRIEF DESCRIPTION OF THE DRAWINGS

Other objects and features of the present invention will become apparent from the following detailed description considered in connection with the accompanying drawings which disclose examples of the present invention. It should be understood, however, that the drawings are designed for the purpose of illustration only and not as a definition of the limits of the invention.

DETAILED DESCRIPTION OF THE INVENTION

Figure 2:
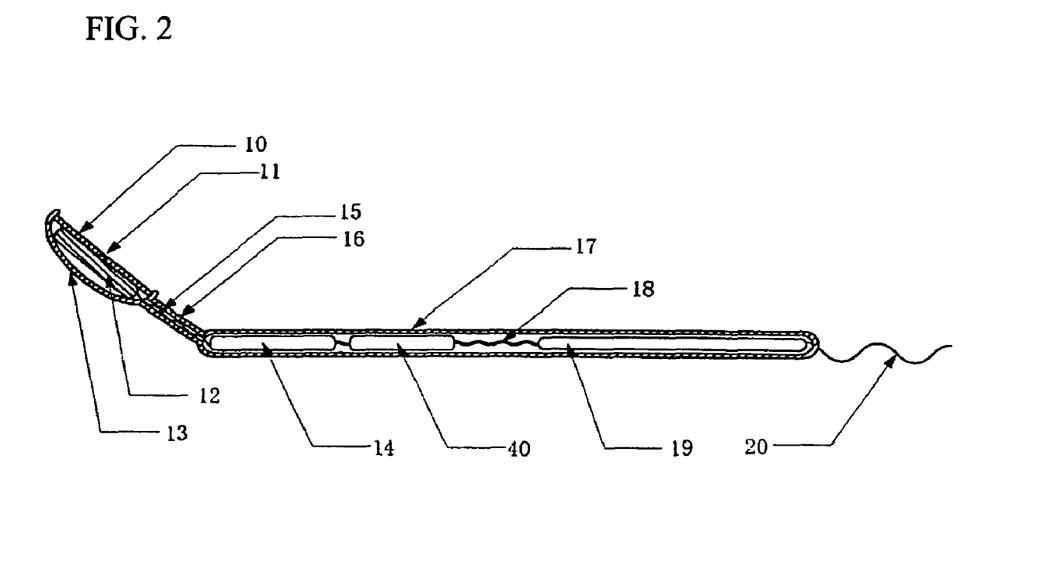
FIG. 2 is a cross sectional view of a dental mirror with a built-in CCD camera.
Figure 3:
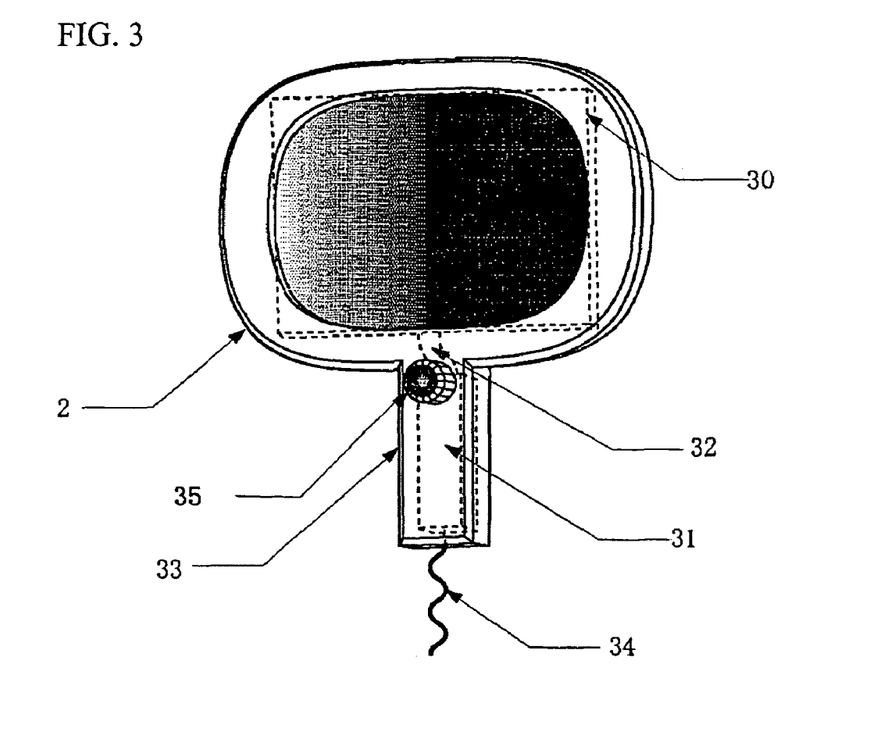
FIG. 3 is a front view of a hand mirror monitor having a cordless CCD camera.

Several examples of the present invention are described herein by incorporating the drawings. FIG. 2 is a working example of the present invention in which the same reference symbols designate the same component. In the example illustrated in FIG. 2, a CCD camera rotation unit 12 is attached to a point inside rear mirror head cover 13 attached to reflector 10 of the dental mirror and a light transmitting aperture 11 is formed in the center of reflector 10, which is the lens thereof, to capture the image of an object in front of the dental mirror. This image is converted to image data by the CCD camera board with a battery 14 provided inside body handle 17 and connected to CCD camera board connection cable 15 in shank 16 and transmitted by transmitter 19 through transmission antenna 20 via CCD camera board and transmitter connecting cable 18.

Figure 8:
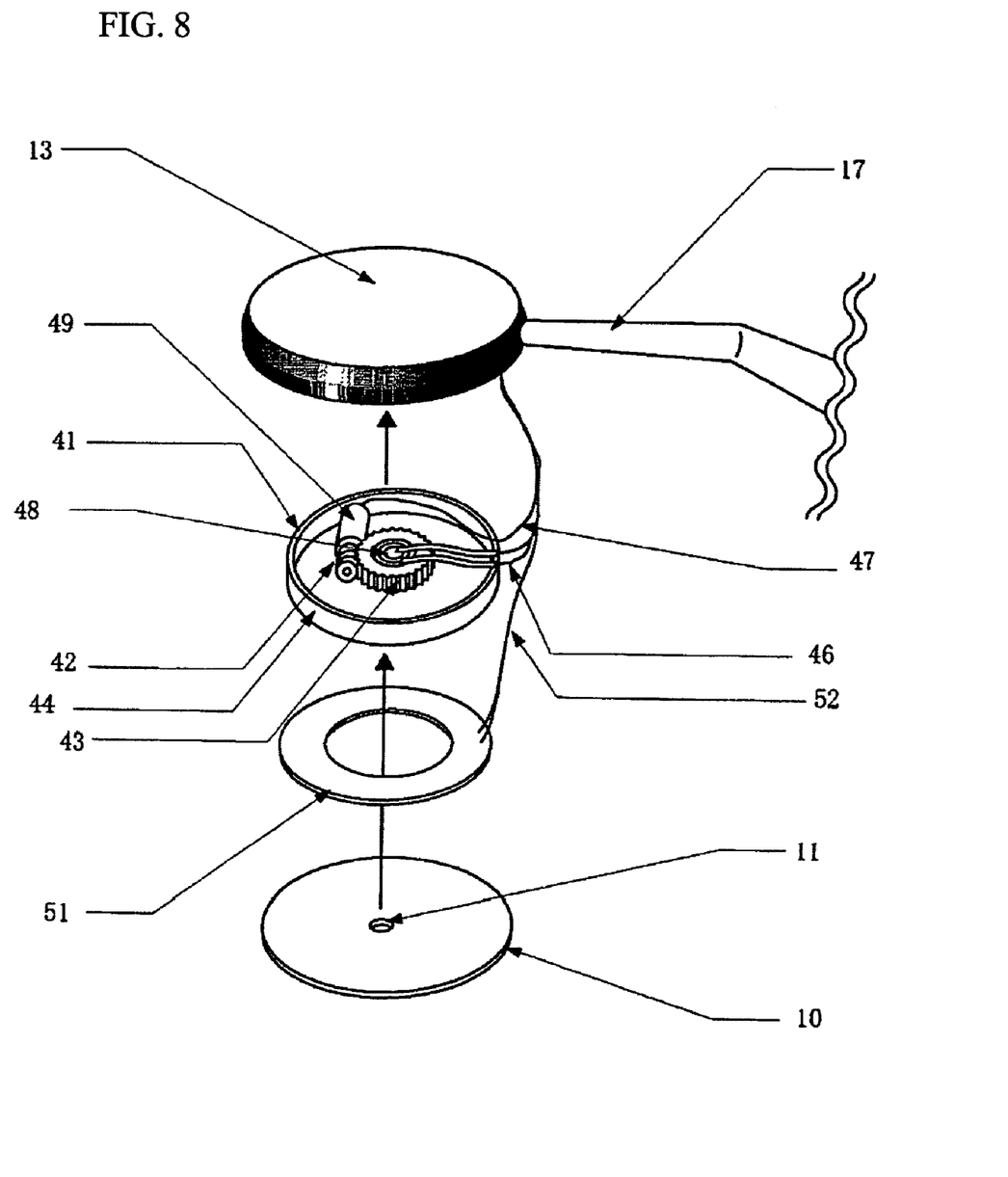
FIG. 8 is a perspective view illustrating a mirror portion being disassembled.

In the CCD camera 48, as illustrated in FIG. 8, a gyro sensor is attached to a point in body handle 17 and controller 40 together drive micro motor 49 to a predetermined position to be rotated. As a result, CCD camera 48 on CCD camera rotation gear 43 automatically rotates to an appropriate angle via worm gear 42.

Further, defogging heater 51 attached between dental mirror surface 44 and CCD camera motor driving unit 44 helps capture a clear image without collecting moisture on dental mirror surface 44 and the light transmitting aperture. The clear image data sent from the CCD camera is thus received by receiving antenna 34 of hand mirror shaped LCD monitor 2, which is then processed by the set of LCD and CCD circuit boards, and receiver and battery 31 built into body holder 33 to be displayed on LCD 30.

Figure 7:
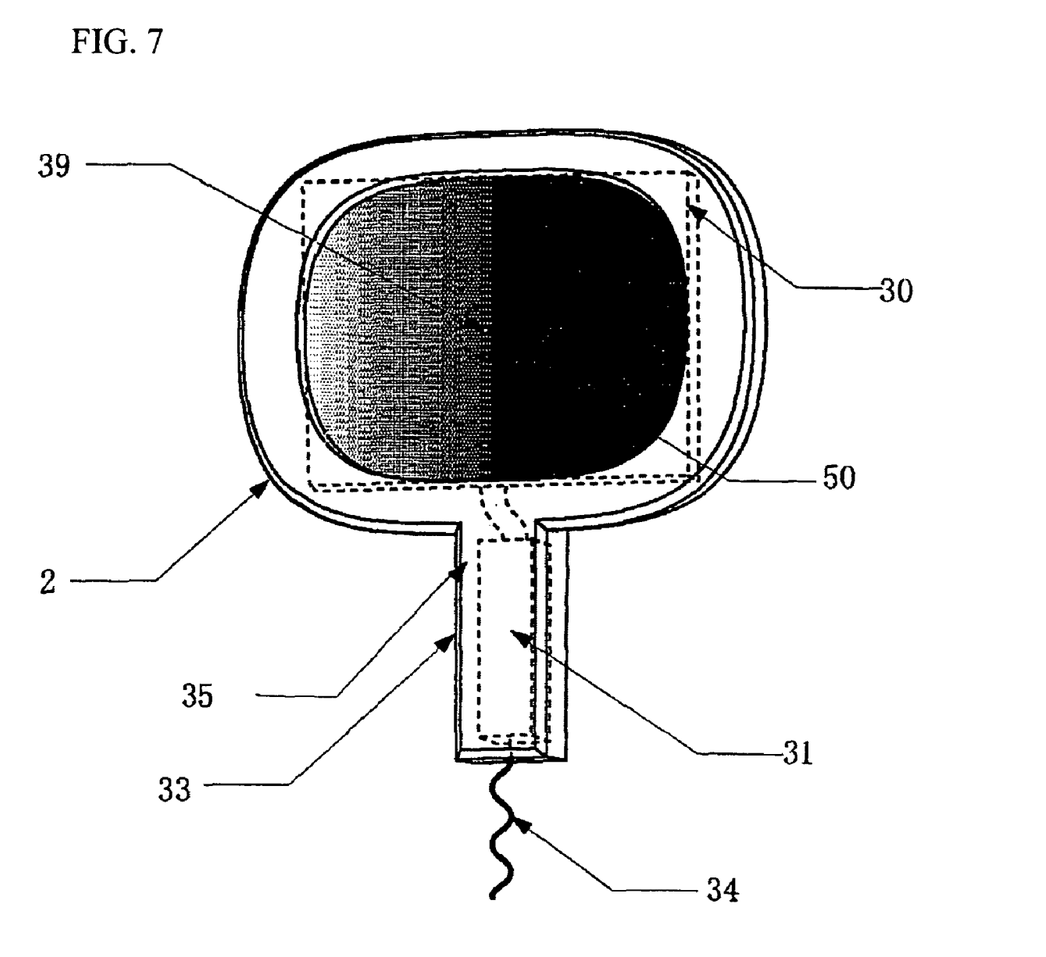
FIG. 7 is a front view of a hand mirror type monitor with a cordless pinhole CCD camera.

As illustrated in FIG. 7, hand-mirror type LCD monitor 2 can be used in the same manner as a generic hand mirror is used by switching CCD camera 50 attached to the back surface of light transmitting aperture 39, which is the center portion of LCD 30 of front body holder 33. It is possible to use an image conversion unit to freely invert the image data of CCD camera 50 upside down or backside forward or clockwise or counterclockwise, thereby providing not only an inverted image, which a hand mirror provides, but also other versions of the image.

Figure 4:
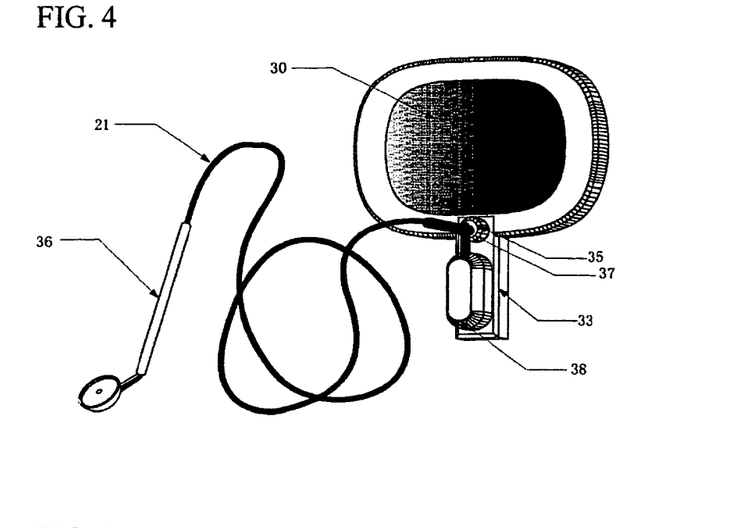
FIG. 4 is a diagram illustrating another example of the present invention which uses optical fiber dental mirror, CCD camera, and a hand mirror type monitor with a light source.
Figure 5:
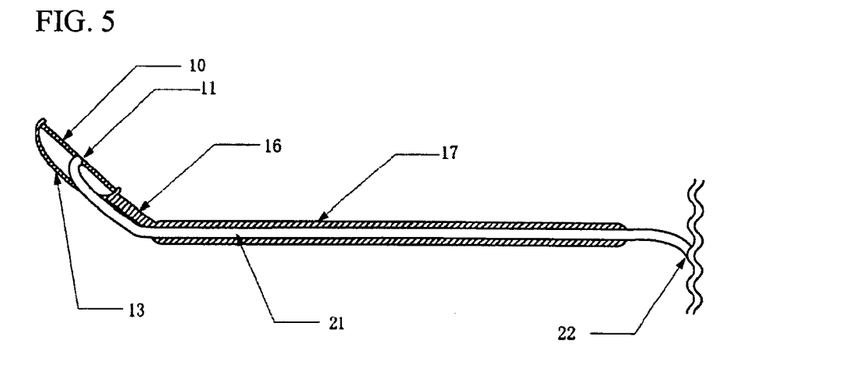
FIG. 5 is a cross sectional view of a dental mirror with a built-in optical fiber.

Alternately, CCD camera 35 can directly project data from inside the mouth onto LCD 30 utilizing optical fiber 21 as illustrated in FIG. 4. The incident portion of optical fiber 21 is attached to light transmitting aperture 11 of dental mirror reflector 10 as illustrated in FIG. 5. CCD camera 35 captures the image inside the mouth within the field of view at the incident portion and displays the digital image thereof on LCD 30 via optical fiber 21, which is more flexible than coaxial optical cable 22 wherein CCD camera 35 is connected to body handle 17 via shank 16. In contrast to the previous type illustrated in FIG. 2, light source unit 38 illuminates light at optical fiber light source incident portion 37 through light transmitting aperture 11 in the system. The dentist thus illuminates the operating area in the mouth.

Figure 6:
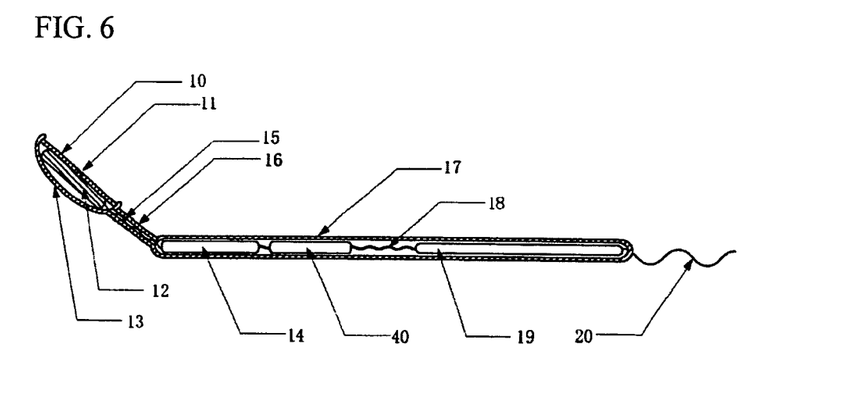
FIG. 6 is a cross sectional view of a dental mirror with a built-in defogging device.

To prevent the dental mirror illustrated in FIGS. 2 and 5 from collecting moisture, suction line hose 27 is connected to a compressor, as shown in FIG. 6, such that air is injected onto the surface of reflector 10 and light transmitting aperture 11 through jet nozzle 23 via exhaust line pipe 26 provided at the side of body handle 17. At the same time, exhaust line hose 28 is connected to a vacuum unit to suck, from suction port 24 via suction line pipe 25 provided on one side of body handle 17, cooling water, saliva, and air injected through jet nozzle 23 onto the surface of reflector 10 and the surface of light transmitting aperture 1.

Operation of the above described examples of the present invention as illustrated in the drawings will be described below.

Dentist 3 uses dental mirror 1 with a built-in CCD camera (hereinafter referred to as "CCD dental mirror 1") in the same way that he or she uses a regular dental mirror, dentist 3 inserts CCD dental mirror 1 into the patient's mouth to observe the area that a patient cannot directly view with reflector 10 as illustrated in FIG. 2, under a surgical lighting system. The light source illuminates the incident direction 7, along line of vision 5 of the dentist. Where the patient is laid horizontally under a surgical lighting system, the angle between line of vision 5 of the dentist using reflector 10 and the line of reflection from the bright field is about 60 degrees.

The angle of view for CCD camera rotation unit 12 attached to the rear surface of light transmitting aperture 11 of reflector 10 is about 100 degrees. Therefore, as long as reflector 10 and the bright field area are separated by 100 mm or more, the field of view reflected by reflector 10 along line of view 5 remains within the angle of view of CCD camera rotation unit 12. The image data stored in CCD camera having a similar field of view as dentist 3 is sent from transmitting antenna 20 to the CCD camera board via CCD camera board connection cable 15, battery 14, and transmitter 19. The data transmitted is received by receiving antenna 34 to be displayed on LCD 30 of hand-mirror type monitor 2, which patient 4 holds at an appropriate position to obtain a bright view along line of view 6 of patient 4 via LCD 30 or CCD circuit board 31, receiver, battery 31 and LCD circuit board connection cable 32.

Figure 1:
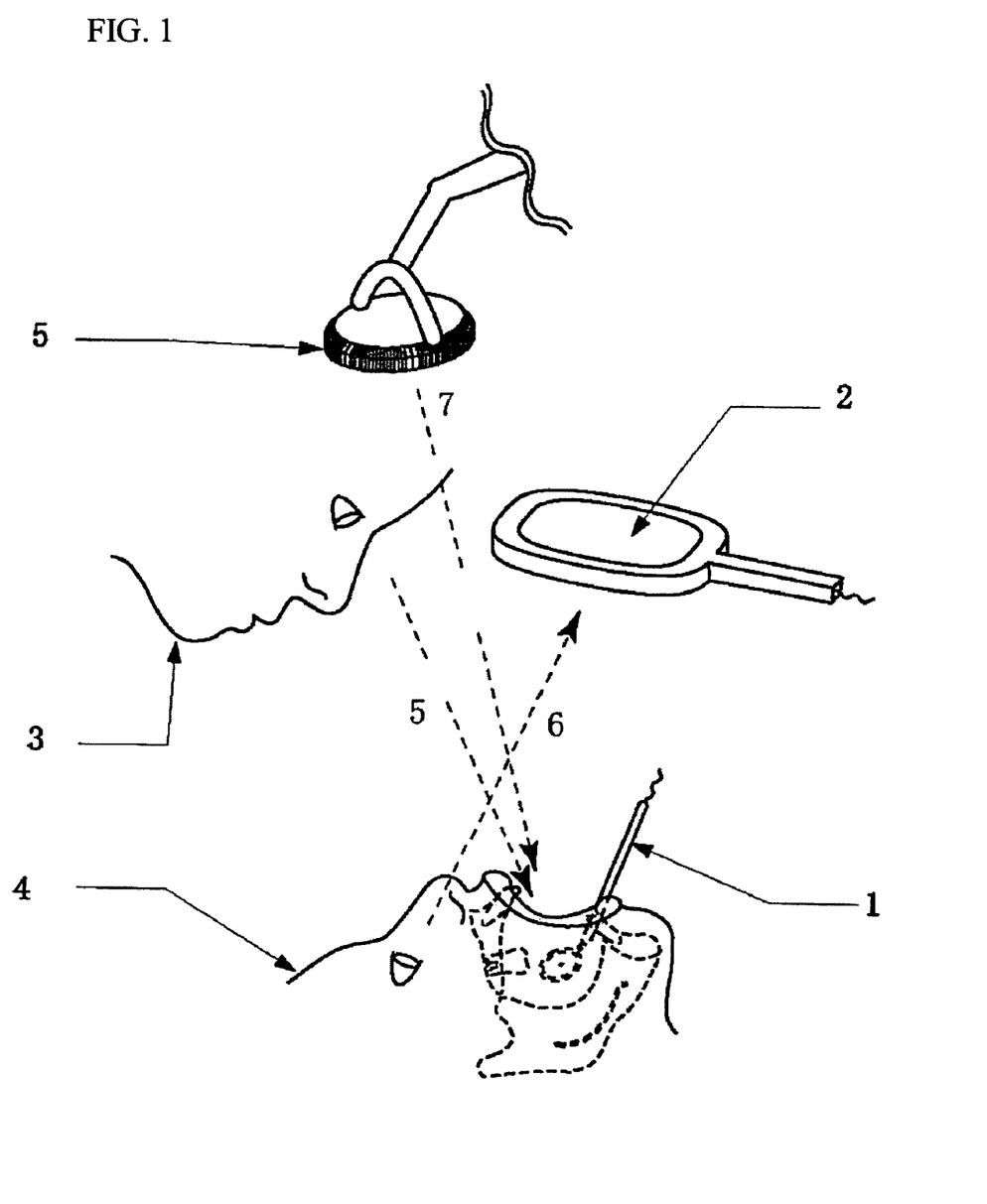
FIG. 1 is a schematic illustration of how the intraoral camera system is used in a clinical situation.

Alternately, the operation of FIG. 1 applies to the intraoral camera system utilizing optical fiber 21 illustrated in FIGS. 4 and 5. Dentist 3 does nothing but operates dental mirror 36 with a built-in optical fiber (hereinafter referred to as "optical fiber dental mirror 36") in the same way that he or she uses a regular dental mirror along line of view 5 of dentist 3 to cause CCD camera 35 attached to holder 33 to form a data image in the field of view of light transmitting aperture 11 of optical fiber dental mirror 36, received via optical fiber 21 to be displayed on LCD 30 of hand mirror type LCD monitor 2. Patient 4, therefore, can clearly see the area, which he or she is unable to see by holding hand-mirror type LCD monitor 2 at an appropriate position, along line of view 6, while lying horizontally on a bed. Dentist 3 can thus provide patient 4 the image which is nearly identical as that clearly viewed in the field of view of reflector 10 of optical fiber dental mirror 36 without looking into another monitor or similar device.

In the mouth, the surface of reflector 10 and light transmitting aperture 11 tend to collect moisture due to the patient's breathing or saliva, the use of cooling water or the like. For a good view, a flow of air may be created in the patient's mouth by injecting air through jet nozzle 23 and vacuuming the air from suction port 24 as illustrated in FIG. 6. Drying of inside the patient's mouth can thus be prevented.

In addition, storing or delivering digital image data through internet or the like help provide standardized medical technology to remote areas, preventing occurrence of malpractice, thereby enhancing evidence based medicine (EMB) policy.

Although the present invention applies to a CCD dental mirror, applications are not limited to the CCD camera, jet nozzle, suction port, optical fiber, the shape of optical fiber cable, hand-mirror type LCD monitor, and transmission means from the CCD dental mirror and delivery means are not limited to these embodiments illustrated in the drawings either. These embodiments may be modified in anyway possible as long as the spirit of the present invention is maintained.

What is claimed is:

1. An intraoral camera system comprising:
   a dental mirror including a reflector having a light transmitting aperture provided in the center or in any other portion of the reflector for transmitting light therethrough,
   a first CCD camera secured in a position adjacent to a back surface of the reflector with an incident portion of said first CCD camera being adjacent to and in optical communication with the light transmitting aperture of the reflector,
   a transmitter connected to said first CCD camera for transmitting an image captured by said first CCD camera, and
   a visual monitor for displaying the image captured by said first CCD camera as transmitted by the transmitter, and
   further comprising:
   the visual monitor being a liquid crystal plate having a light transmitting aperture at the center where some liquid crystal material is removed to transmit light therethrough, and
   a second CCD camera provided on a back surface of the liquid crystal plate with an incident portion of said second CCD camera being adjacent to and in optical communication with the light transmitting aperture,
   whereby an object located in front of said second CCD camera may alternatively be displayed on said visual monitor in the same manner that a generic hand mirror displays the object.

2. The intraoral camera system as set forth in claim 1 further comprising a server for storing image data captured by said first CCD camera and outputting the image data as required to project the stored image data on the monitor on an as needed basis.

3. The intraoral camera system as set forth in claim 1, wherein the monitor is made in the form of a hand mirror such that said first CCD camera image data received can be viewed without changing the patient's position.

4. The intraoral camera system as set forth in claim 1, which further comprises an image conversion processor for inverting data input from said second CCD camera at the center of said visual monitor upside down or backside forward or counterclockwise or clockwise.

5. The intraoral camera system as set forth in claim 1 further comprising a heater provided at a position in the dental mirror where the heater does not shield the incident portion of said first CCD camera but inhibits fogging of the reflector and the incident portion of said first CCD camera due to breathing by a patient.

6. The dental mirror as set forth in claim 1 further comprising:
   a light source in optical communication with the light transmitting aperture in said dental mirror for illuminating the target area in the patient's mouth.

7. An intraoral camera system comprising:
   a dental mirror including a reflector having a light transmitting aperture provided in the center or in any other portion of the reflector for transmitting light therethrough,
   a CCD camera secured in a position adjacent to a back surface of the reflector with an incident portion of the CCD camera being adjacent to and in optical communication with the light transmitting aperture of the reflector,
   a transmitter connected to the CCD camera for transmitting an image captured by the CCD camera, and
   a visual monitor for displaying the image captured by the CCD camera as transmitted by the transmitter,
   wherein the CCD camera is rotatably attached to the center of the back surface of the reflector, and
   wherein the dental mirror further comprises
   a gear attached to a same rotary shaft as that of the CCD camera such that the gear rotates around the CCD camera,
   a micromotor provided on the back surface of the reflector such that the motion of the micromotor is incorporated with that of the gear,
   a battery provided inside a holder for the reflector for driving the micromotor, a gyro sensor provided inside the holder for outputting a signal associated with an angle of inclination of the dental mirror to a horizontal plane, and a controller for driving the micromotor in accordance with the signal from the gyro sensor to control rotation angles of the CCD camera, thereby allowing an image captured at a preset angle to be displayed regardless of the angle at which a dentist holds or insert the dental mirror into the patient's mouth.

8. The intraoral camera system as set forth in claim 7 further comprising a server for storing image data captured by the CCD camera and outputting the image data as required to project the stored image data on the monitor on an as needed basis.

9. The intraoral camera system as set forth in claim 7, wherein the monitor is made in form of a hand mirror such that the CCD camera image data received can be viewed without changing the patient's position.

10. The intraoral camera system as set forth in claim 7 further comprising a heater provided at a position in the dental mirror where the heater does not shield the incident portion of the CCD camera but inhibits fogging of the reflector and the incident portion of the CCD camera due to breathing by a patient.

11. The dental mirror as set forth in claim 7 further comprising:

a light source in optical communication with the light transmitting aperture for illuminating the target area in the patient's mouth.

12. A dental mirror comprising:

a reflector having a light transmitting aperture provided in the center or in any other portion of the reflector for transmitting light therethrough, a CCD camera secured in a position adjacent to a back surface of the reflector with an incident portion of the CCD camera adjacent to and in optical communication with the light transmitting aperture of the reflector, a gear attached to a same rotary shaft as that of the CCD camera such that the gear rotates around the CCD camera, a battery driven micromotor, a battery positioned inside the dental mirror, a gyro sensor for outputting a signal that incorporates a motion of the gyro sensor with that of the gear on inclination of the dental mirror to a horizontal plane or floor, and a control mechanism for controlling the rotation angle of the CCD camera in accordance with the signal from the gyro sensor.

13. A dental mirror equipped with a CCD camera comprising:

an optical fiber having its one end located in such a manner that an incident portion thereof is at a light transmitting portion of a dental mirror a part of which surface allows light to transmit therethrough, which fiber is coaxially with, or passes through, a retainer portion of said dental mirror, the other end of the optical fiber being provided with a CCD camera for capturing image data at the incidence portion of said dental mirror, and a hand mirror shaped monitor having an illumination light source for projecting the target image of said camera;

wherein the field of view obtained at said optical fiber's incident portion is captured by the CCD camera in said hand mirror shaped monitor and is displayed on the hand mirror monitor and, at the same time, the light from the illumination light source of the hand mirror shaped monitor is projected in the direction in which the dental mirror captures the image, and wherein the optical fiber is made detachable such that, when the optical fiber is removed, the image in front of the hand mirror monitor is displayed by the CCD camera thereby providing a hand mirror monitor which can be used just like a reflector hand mirror.

14. The dental mirror equipped with a CCD camera as set forth in claim 13 further comprising:

a hose made of a flexible material that is connected to a compressor, an air exhaust pipe one end of which is connected to said hose and the other end being provided with a jet nozzle pointed toward the optical fiber's incident portion, an additional hose made of a flexible material that is connected to a vacuum device, an air suction pipe with one end thereof connected to said additional hose and with the other end having a suction inlet located at a point which is suited to suck in the air exhausted from the jet nozzle, said dental mirror provided in such a manner that the suction pipe and the exhaust pipe are coaxial with, or pass through, the retainer portion wherein air is ejected to the mirror surface while sucking air therefrom to provide an air curtain effect, thereby preventing patients mouth cavity from drying and preventing the mirror surface from fogging.

15. An intraoral camera apparatus adapted to assist a doctor or dentist to obtain informed consent from their patient by providing a visual aid that allows the patient to view, regardless of their body position, the area in the patient's mouth which the patient cannot see with only a single reflector, said intraoral camera apparatus comprising:

a dental mirror with a mirror surface for use with dental treatments;

a first CCD camera attached to a back surface of said dental mirror and having an incoming light portion provided in a portion of the mirror surface of the dental mirror; said dental mirror with said first CCD camera attached thereto adapted to be held by one hand of the doctor or dentist and to be inserted into the patient's mouth to observe the area that the patient cannot directly view with the reflector;

a hand mirror shaped LCD monitor, having a light transmitting aperture at the center where some liquid crystal material is removed to transmit light therethrough, adapted to be held by the patient so that the patient may move the hand mirror shaped LCD monitor to any desired position without moving his or her head when viewing the video image, said hand mirror shaped LCD monitor for displaying thereon a video image similar to an image captured through reflection from the mirror surface of the dental mirror, when the video image captured with the CCD camera is received wire or wireless and displayed on the hand mirror shaped LCD monitor for informed consent by the patient; and a second CCD camera provided on said hand mirror shaped LCD monitor;

whereby an object located in front of said second CCD camera may alternatively be displayed on hand mirror shaped LCD monitor in the same manner that a generic hand mirror displays the object.

16. A intraoral camera apparatus according to claim 15 further comprising a server for saving the video image captured by the CCD camera and providing the video image as its output to the hand mirror shaped LCD monitor whereby the video image is displayed on the monitor from time to time.

17. A intraoral camera apparatus according to claim 15 further comprising an air curtain device for removing moisture from the mirror surface of the dental mirror and preventing drying up of the patient mouth, the air curtain device comprising an injection pipe, a suction pipe and a vacuum machine connected with the injection and suction pipes, said dental mirror having an elongated handle with said mirror surface at an end of said handle, said injection and suction pipes leading from said mirror surface along said elongated handle to said vacuum machine.

* * * * *